United States Patent [19]

Wieder et al.

[11] 4,102,574

[45] Jul. 25, 1978

[54] METHOD AND MEANS OF MONITORING THE QUALITY OF A FLUID DIELECTRIC

[75] Inventors: Herman H. Wieder; Neil M. Davis, both of San Diego, Calif.

[73] Assignee: The United States of America as represented by the Secretary of the Navy, Washington, D.C.

[21] Appl. No.: 795,690

[22] Filed: May 11, 1977

[51] Int. Cl.² ............................................. G01N 21/40
[52] U.S. Cl. ................................................. 356/117
[58] Field of Search ...................... 356/114, 116, 117; 350/147, 150

[56] References Cited

U.S. PATENT DOCUMENTS

| 2,998,751 | 9/1961 | Granqvist | 350/150 |
| 3,411,342 | 11/1968 | Liermann | 356/116 |

OTHER PUBLICATIONS

Nalbandov, L. V., "Photoelectric Apparatus for Measuring Absolute Kerr Constants"; Measurement Techniques, Nov. 1970, pp. 1636–1638.

Primary Examiner—John K. Corbin
Assistant Examiner—R. A. Rosenberger
Attorney, Agent, or Firm—R. S. Sciascia; G. J. Rubens; T. M. Phillips

[57] ABSTRACT

A method and means of monitoring the quality of a fluid dielectric capacitor by measuring the Kerr signal of a dielectric fluid which has the desired dielectric and breakdown properties and continually measuring the Kerr signal of the same fluid dielectric while in use to determine if there is any degradation of the fluid in use. The means for measuring the Kerr signal is by projecting a high intensity light beam such as from a laser source through the dielectric fluid of a capacitor between two of the plates and detecting the amount of light passed through the dielectric which is an indication of the condition of the dielectric liquid.

7 Claims, 3 Drawing Figures

4,102,574

METHOD AND MEANS OF MONITORING THE QUALITY OF A FLUID DIELECTRIC

BACKGROUND OF THE INVENTION

Where oil-filled capacitors in high power VLF transmitters, such capacitors are prone to catastrophic failure due to breakdown of the oil. Such breakdown is induced by decomposition of the oil. The age/use induced change in the dielectric properties then should be determined early enough so that the oil can be changed before catastrophic damage sets in. Technicques in use at this time employ cumbersome and relatively inaccurate methods for determining the quality of dielectric fluids such as petroleum-derived oils. The Perelli test measures the quantity of hydrogen and hydrocarbon gases evolved or absorbed under high electric field stress. As discussed by A. A. Zacky and I. Y. Megahed, Transaction Electrical Insulation, EI-7, 145 (1972). Another technique is one which determines the fractional content of unsaturated aromatics present in the oil. Such aromatics of which benzene, naphathalene or anthracene are typical, tend to absorb hydrogen, ethane, propane, etc., preventing the formation of gas bubbles. Such bubbles tend to ionize in electric fields of 30 to 50 kV/cm initiating the decomposition of the oil and ultimately its catastrophic breakdown. Nuclear magnetic resonance and proton magentic resonance, techniques have been employed to determine the concentration of unsaturated aromatics in commercially available oils. The apparatus required for these tests is expensive, bulky and not suitable for on-line monitoring of the properties of insulating oils.

SUMMARY OF THE INVENTION

The present invention provides a method and means of a simple procedure based on the Kerr effect that is suitable for determining the fractional aromatic content of various oils and is inexpensive in comparison with prior known techniques and is suitable either for on line or for remote sampling of oil specimens. The Kerr signal is measured by providing a monochromatic light source such as a helium-neon laser providing a well-collimated beam of light applied to a polarizer for making the light plane-polarized. The light beam is passed through a window of the oil filled casing of the capacitor in such a way that the light traverses the space between two capacitor plates. The light emerges through a window in the opposite wall of the capacitor case, is passed through a second polarizer and is detected by means of a photo detector. The amount of light detected is an indication of the quality of the liquid dielectric of the capacitor being monitored.

Accordingly, an object of the invention is the provision of a method and means of monitoring the quality of a fluid dielectric for a capacitor.

Other objects and many of the attendant advantages of this invention will be readily appreciated as the same becomes better understood by reference to the following detailed description when considered in connection with the accompanying drawings.

DESCRIPTION OF THE PREFERRED EMBODIMENTS

Figure 1:
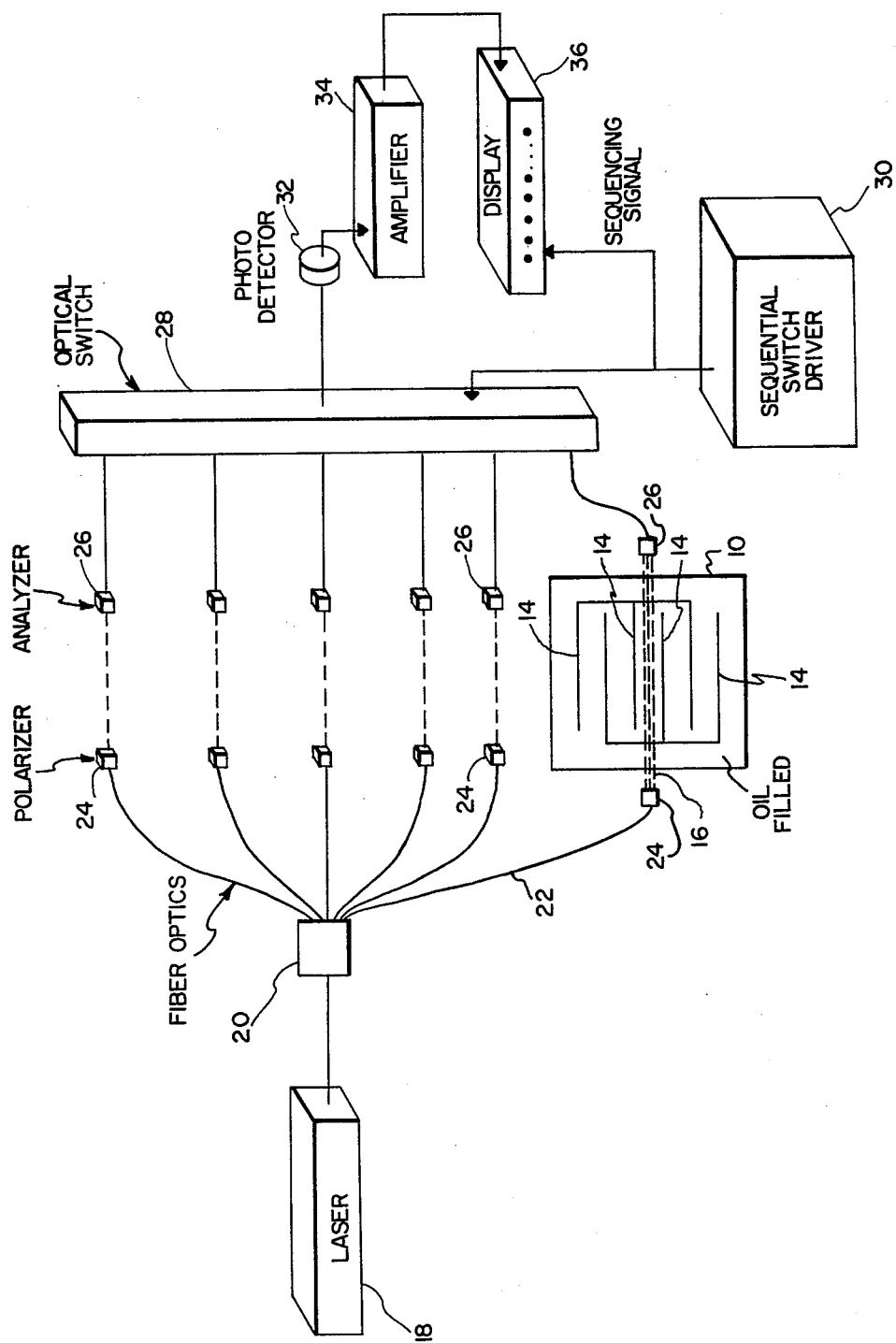
FIG. 1 is a preferred embodiment of the invention.

Referring now to FIG. 1 wherein there is shown schematically the apparatus used in monitoring the quality of the liquid dielectric in capacitor 10. A monochromatic light source such as a monochromatic light source 18, such as a helium-neon laser providing a well collimated beam of light is fed to an optical multi-coupler 20 and is fed by means of fiber optic cables 22 to polarizers 24. The light beam is then introduced into the oil filled capacitor by means of an aperture (not shown) containing the insulated fluid in which are immersed the parallel metallic plates 14 of the capacitor 10. The light beam 16 traverses through the dielectric fluid between the plates 14. It propagates at 45° with respect to the electric field generated by an alternating potential by way of example 10 to 20 kC an amplitude of up to 15 kV (RMS) applied to the capacitor plates from a source, not shown. The light then traverses a second polarizing prism 26, identical to the polarizing prism 24. The plane of polarization of polarizer 26 is oriented at 90° with respect to that of polarizer 24 and both are oriented at 45° with respect to the plane of the electric field of the Kerr cell formed by the capacitor plates 14 and the liquid dielectric in accordance with the well known Kerr cell theory.

The normally optically isotropic fluid in the capacitor between the capacitor plates becomes birefringent in the applied electric field. No light propagates beyond polarizer 26 if the applied field is 0. The induced birefringence of the liquid in the capacitor renders the light elliptically polarized and the ellipticity is a function of the applied field in accordance with the Kerr cell theory.

Kerr's law relates the optical path difference in a Kerr cell to the applied electric field E in terms of $$n_p - n_s = K\lambda E^2 \tag{1}$$

where $K$ is a constant of proportionality defined as Kerr's constant and $l$ is path length through the liquid. The theory of the Kerr effect commonly accepted at present relates the intrinsic electrooptical polarizability of a molecule to its Kerr constant K. It is strictly applicable only to gases or to materials which can be vaporized without decomposition. However, it can be applied, with a first order approximation, to liquids.

The phase angle between the parallel and perpendicular components of the elliptically polarized light is $\phi = 2\pi\Delta/\lambda$ and in terms of equation (1)

$$\phi = 2\pi K l E^2 = (2\pi l/\lambda) \cdot (n_p - n_s) \tag{2}$$

The sinusoidal potential from a high voltage source (not shown), $v = v_o \cos\omega t$ is applied to the capacitor plates. Let the effective field, $E = v/d$. $d$ is the distance between plates 14. Birefringence is induced in the fluid and the elliptically-polarized light emerges from the fluid passes through the polarizer 26.

The planes of polarization of 24 and 26 are orthogonal to each other and at an angle of 45° with respect to E;

$$\alpha = 45°$$

$$\beta = 90° + 45°.$$

The elliptically-polarized light in the liquid may be represented by the components $I_o \cos\alpha$, parallel to E, and $I_o \sin\alpha$, perpendicular to E. When these components strike the analyzer each generates two additional components:

$$I_o \cos\alpha \cdot \cos\beta$$

$$I_o \sin\alpha \cdot \sin\beta$$

parallel to the plane of the polarization of the analyzer, and $$I_o \cos\alpha \cdot \sin\beta$$

$$I_o \sin\alpha \cdot \cos\beta$$

perpendicular to the plane of the analyzer. Only the two parallel components are transmitted by the analyzer. A spatial phase angle $\phi$ is considered to exist between these two components.

The transmitted intensity $I_t$ is $$I_t = I_o \sin^2(\phi/2) = (I_o/2)(1 - \cos\phi) \approx (I_o/2) \cdot (\phi^2/2) \qquad (3)$$

Let $E = E_o \cos\omega t$, then from Equations (2) and (3):

$$I_t = I_o \pi^2 K^2 l^2 E_o^4 \cdot \cos^4\omega t = (kE_o^4 K^2/2)(1 + \cos 2\omega t)^2 \qquad (4)$$

where $k = I_o \pi^{2} l^2$ and Equation (4) is $$I_t = (kK^2 E_o^4/4)[3 + 4\cos 2\omega t + \cos 4\omega t] \qquad (5)$$

The light intensity emerging from the polarizer 26 thus has a steady-state component, a second harmonic component and a fourth harmonic component. It is proportional to the fourth power of the peak applied field and quadratically to the Kerr coefficient. The Kerr coefficient K of a pure fluid is a function of variables such as the temperature T, molecular density $\nu$, wavelength of the light $\lambda$ and of specific material parameters such as the isotropic (E = 0) index of refraction of the fluid $n$, its dielectric constant $\epsilon$, the electro-optical anisotropy of the molecular polarizability $\theta_1$ which is a function of the reciprocal temperature, and the orientation of the permanent molecular dipoles, $\theta_2$ which is a function of the reciprocal of the square of the absolute temperature:

$$K = \frac{\pi\nu(n^2 + 2)^2(\epsilon + 2)^2}{27n\lambda} (\theta_1 + \theta_2) \qquad (6)$$

The Kerr electro-optic effect can be used for comparing, by substitution, the properties of different insulating fluids. Let the light intensity $I_t$ emerging from the polarizer 26, in FIG. 1, induce a proportional signal, S in the photoelectric sensor 32. Then, in accordance with Equation (4):

$$S = k_1 K^2 E_o^4 \cos^4\omega t \qquad (7)$$

where $k_1$ is a constant. In consequence of Equation (6), S may be expected to have a parametric dependence on the material parameters $K(n, \epsilon, \theta_1, \theta_2)$ which are specifics of the oil. The index of refraction may be considered to represent the contribution of the electronic polarization to the total polarization while $\epsilon$ is presumed to represent the low frequency, dipole and ionic contributions.

It is considered that corona and breakdown of mineral oils used in high voltage capacitors are initiated by the formation of gas bubbles or by trapping of air bubbles between the capacitor plates. The total electrostatic energy stored in an insulating fluid having a dielectric constant, $\epsilon$ in which a spherical air bubble of volume $v$ is trapped is $$E_s = \frac{1}{8\pi} \int_v (\epsilon - 1) E_o E_1 dv \qquad (8)$$

where $E_o$ is the applied field and $E_1$ is the effective field in the air bubble. $E_s$ will tend to decrease in accordance with the principle of minimum free energy; the initially spherical bubble will be distorted into a prolate ellipsoid whose major axis is directed along the field. Beyond a critical elongation, controlled by $E_o$, the bubble may fission breaking up into smaller bubbles which may diffuse to the surface of the oil or attach themselves to the metal electrodes. Alternatively, if $E_1$ exceeds the breakdown strength of the air in the bubble reaching values of 30 to 50 kV/cm, the air or gas may become ionized cresting a luminous corona discharge. Ions and energetic electrons from the ionized bubble can decompose the oil by creating free radicals which release hydrogen, methane and other gases in the form of bubbles continuing the process of breakdown. They may also cause polymerization of some of the oil and the formation of carbon precipitates. It appears that oils containing a higher fraction of unsaturated aromatics can quench corona or prevent a discharge from developing into a catastrophic breakdown.

Figure 2:
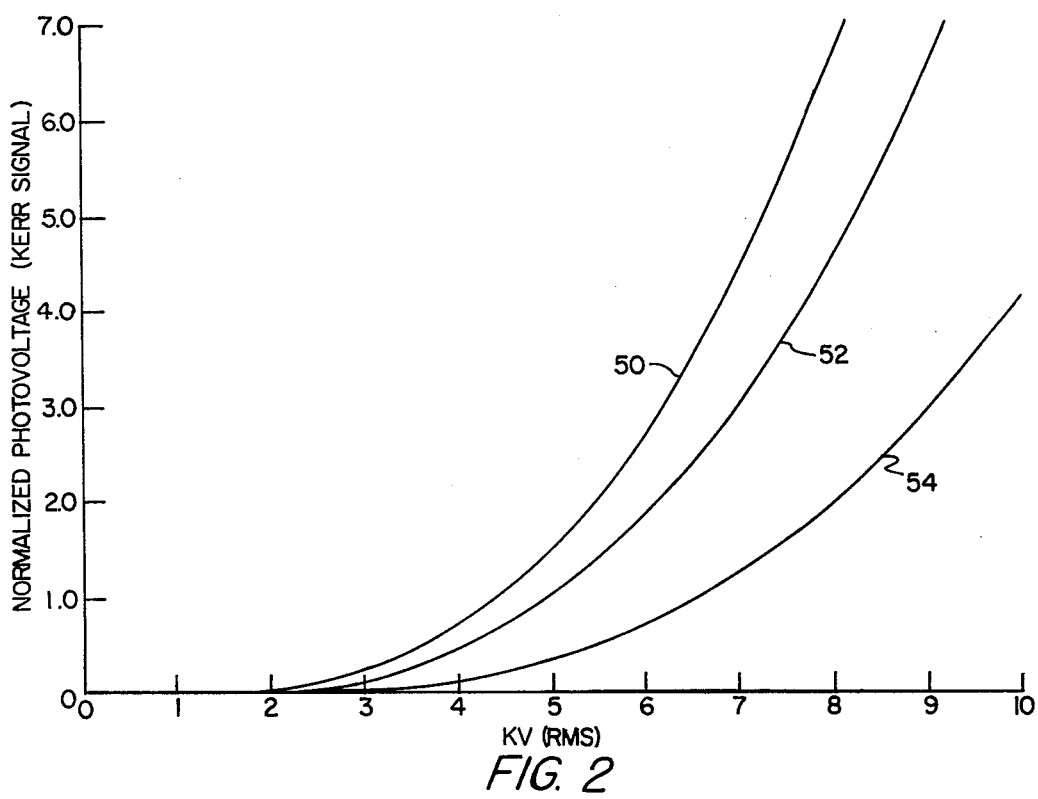
FIG. 2 is a graph of typical measured curves of the dependence of the Kerr signal on the RMS value of a sinusoidal potential of 15 KHz applied to a Kerr cell.

By using a Kerr cell and keeping all parameters constant, the signal S was measured as a function of the root mean square applied voltage between 0 to 10 kv at 13 kHz; this corresponds to a peak applied field, $E_o = 70.5$ kV/cm. The dependence of S on E for various oils is shown in FIG. 2. A comparison of the data shown in FIG. 2 with that of Table I shows qualitative agreement.

TABLE I

| SAMPLE | % AROMATIC $C^{13}$ | Normalized Kerr Signal |
|---|---|---|
| New CHEVRON Insulating Oil | 3.54 | 0.30 |
| EXXON 1830 New | 5.6 | 0.37 |
| C-2502 Lualualei | 5.66 | 0.50 |
| Rodman CZ, New Oil (FA 1182) | 7.3 | 0.50 |
| NORWAY - Oldest stock | 8.54 | 0.80 |
| Rodman CZ, oil in use (FA 1184) | 8.7 | 0.82 |
| EXXON Univolt 33, New | 8.9 | 1.00 |
| NORWAY - PA 2 Capacitor C-4 | 9.05 | 0.78 |
| Rodman CZ, old used oil (FA 1183) | 9.2 | 0.64 |
| TEXACO-55 BTEW 01854 | 9.8 | 1.00 |
| Drum 18 TEXACO-55 BTEW 08285 | 9.95 | 1.05 |
| No marking on drum (TEXACO-55?) | 10.0 | 1.05 |
| EXXON Univolt 35 New | 10.4 | 1.22 |
| Used Oil Yosami Station | 10.98 | 1.21 |
| New Oil Yosami Station | 11.55 | 1.45 |
| Used JAPAN ESSO No. 2 | 12.8 | 1.52 |
| New JAPAN ESSO NO. 2 | 13.4 | 1.50 |

The elliptically polarized light passes through polarizer 26 and is fed by means of fiber optic cables to the optical switch 28. Optical switch 28 is sequentially switched in order that monitoring of a number of capacitors may be accomplished in remote locations. Light passed through optical switch 28 is coupled by means of fiber optics to a photodetector 32 in which it induces a signal proportional to the transmitted light intensity $I_t$.

In accordance with Kerr cell theory the Kerr signal $$S = K^2 \cdot C(3E_o^4 \cos 2\omega t + E_o^4 \cos 4\omega t)$$

where $C$ is a constant of proportionality, $E_o$ is the peak value of the AC field and $K$ is a material parameter, specific of the fluid in the Kerr cell. The Kerr signal, S and the photodetector 32 therefore consist of a DC component, a second harmonic component and a fourth harmonic component. Amplifier 34 is tuned to the second harmonic of the alternating potential applied to the capacitor plates.

As shown in FIG. 2 there is a dependence of the Kerr signal on the rms value of a sinusoidal potential applied to the plates of the Kerr cell.

Curves 50, 52 and 54 are for different insulating fluids used in a Kerr cell. Table I lists their relative Kerr signals measured and (rms) field of 15 kHz and 25 kV/cm compared against their $C^{13}$ unsaturated aromatic content measured by NMR.

Figure 3:
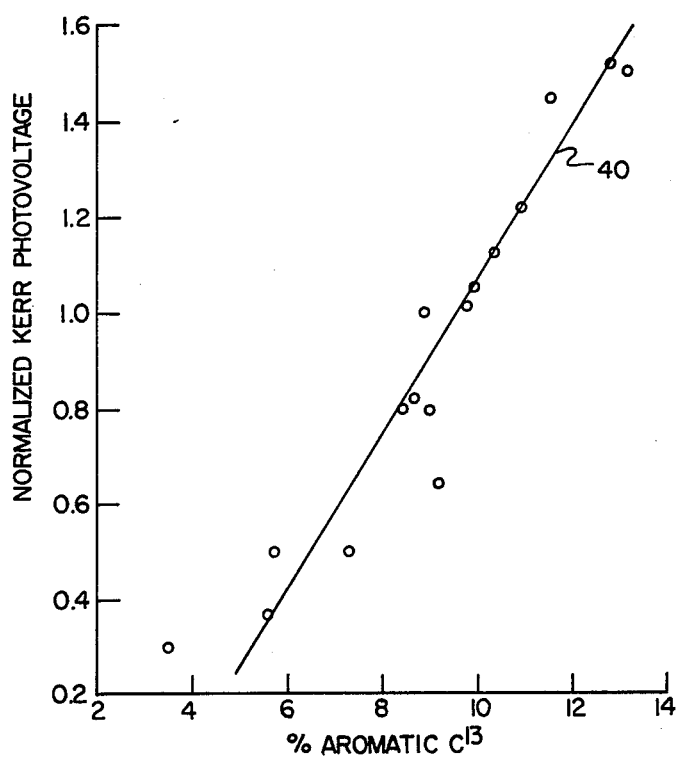
FIG. 3 is a graph showing the linear dependence between the Kerr signals and the unsaturated aromatic contents of various oils.

FIG. 3 shows that there is a linear dependence between the Kerr signals and the unsaturated aromatic content of various oils from table I. From FIGS. 3 and Table I it is shown that deterioration or degradation of insulating fluids and use can be measured in terms of the decrease in Kerr signal, S for a fixed electric field in comparison with the same virginal specimen. The amplified signal out of amplifier 34 is fed to a digital display 36 which is synchronized with the optical switch by means of a sequential switch driver 30.

Obviously many modifications and variations of the present invention are possible in the light of the above teachings. It is therefore to be understood that within the scope of the appended claims the invention may be practiced otherwise than as specifically described.

What is claimed is:

1. The method of monitoring the quality of a fluid dielectric for a capacitor, the steps of:
   (a) measuring the Kerr signal of a dielectric fluid of interest which has the desired dielectric and breakdown properties,
   (b) continually measuring the Kerr signal of the same fluid dielectric while in use,
   (c) comparing the continuously measured signals with the initial measured signal to determine the dielectric degradation of the fluid in use.

2. The method of claim 1 wherein the degradation of the fluid in use is determined by the amount of decrease in the Kerr signal measured in the fluid dielectric in use.

3. The method of claim 1 wherein monitoring the quality of the fluid dielectric for more than one capacitor includes the additional step of sequentially measuring the Kerr signal of the fluid dielectrics in use.

4. Apparatus for monitoring the quality of a fluid dielectric of a capacitor comprising:
   (a) a capacitor having a case filled with dielectric fluid and the capacitor plates submerged in said fluid, opposite walls of said case having apertures in alignment with each other,
   (b) a source of high intensity light and a first polarizer positioned adjacent one of said apertures for emitting a plane-polarized high intensity light beam through one of said apertures between two of the plates of said capacitor and through the other aperture,
   (c) a second polarizer and a light detecting means positioned to detect the amount of said light beam that passes through said dielectric field.

5. Apparatus for remotely monitoring the quality of fluid dielectrics in capacitors, the combination of:
   (a) a plurality of capacitors, each having a case filled with dielectric fluid and the capacitor plates submerged in said fluid, opposite walls of each of said cases having apertures in alignment with each other,
   (b) a source of high intensity light,
   (c) fiber optic means coupling said light to one of the apertures in each of said capacitors,
   (d) first polarizing means positioned between the terminating fiber optics and said aperture for permitting a plane-polarized high intensity light beam to pass through the dielectric fluid between two of the capacitor plates and through the other aperture of each of said capacitors,
   (e) a second polarizing means and a light detecting means positioned to detect the amount of said light beam that passes through the second aperture of each of said capacitors.

6. The apparatus of claim 5 further comprising sequential switching means for sequentially coupling the light that passes through the second aperture of each of said capacitor to said detecting means.

7. The apparatus of claim 6 further comprising display means coupled to said detecting means for providing a continuous display of the condition of the fluid through which the detected light passes.

* * * * *